(12) United States Patent
Baron et al.

(10) Patent No.: US 7,718,361 B2
(45) Date of Patent: May 18, 2010

(54) QUANTITATIVE TEST FOR BACTERIAL PATHOGENS

(75) Inventors: Ellen J. Baron, Los Altos, CA (US); Wolf-Dieter Engel, Feldafing (DE); Gerd Haberhausen, Penzberg (DE); Peter Kaspar, Penzberg (DE); Andreas M. Kogelnik, Palo Alto, CA (US)

(73) Assignees: Roche Molecular Systems, Inc., Pleasanton, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 282 days.

(21) Appl. No.: 10/532,319

(22) PCT Filed: Dec. 5, 2003

(86) PCT No.: PCT/US03/38783

§ 371 (c)(1), (2), (4) Date: Apr. 22, 2005

(87) PCT Pub. No.: WO2004/053457

PCT Pub. Date: Jun. 24, 2004

(65) Prior Publication Data

US 2006/0269914 A1    Nov. 30, 2006

(30) Foreign Application Priority Data

Dec. 6, 2002  (EP) ................... 02027272
Apr. 4, 2003  (EP) ................... 03007458

(51) Int. Cl.
C12Q 1/68   (2006.01)
C12P 19/34  (2006.01)
C07H 21/04  (2006.01)

(52) U.S. Cl. ............ 435/6; 435/91.2; 435/92.5; 435/92.51; 536/24.32

(58) Field of Classification Search ............ None
See application file for complete search history.

(56) References Cited

U.S. PATENT DOCUMENTS 5,118,801 A    6/1992   Lizardi et al. ............ 536/27

(Continued)

FOREIGN PATENT DOCUMENTS

EP    0 070 687 B1    10/1985

(Continued)

OTHER PUBLICATIONS

Tyrell, G.J. et al. Species identification of enterococci via intergenic ribosomal PCR. Journal of Clinical Microbiology 35(5):1054-1060 (May 1997).*

(Continued)

*Primary Examiner*—Diana B Johannsen
(74) *Attorney, Agent, or Firm*—Rhea Nersesian (57) ABSTRACT

The present invention is directed to a method for analyzing the presence of a bacterial pathogen in a clinical sample comprising the steps of (i) at least partially isolating nucleic acid from said sample, characterized in that said nucleic acid is selected from a group consisting of either total nucleic acid, total DNA or total RNA, (ii) quantifying the amount of nucleic acid comprising a preselected sequence which is specific for said bacterial pathogen, and (iii) determining whether said amount of nucleic acid comprising a preselected sequence which is specific for said bacterial pathogen exceeds a first predetermined cut off value.

2 Claims, 1 Drawing Sheet

U.S. PATENT DOCUMENTS

| | | | |
|---|---|---|---|
| 5,210,015 A | 5/1993 | Gelfand et al. | 435/6 |
| 5,770,409 A | 6/1998 | Hermann et al. | 436/517 |
| 5,849,488 A | 12/1998 | Alatossava et al. | |
| 6,730,501 B2* | 5/2004 | Eyre et al. | 435/91.2 |
| 7,074,598 B2* | 7/2006 | Cockerill et al. | 435/91.2 |
| 2002/0115077 A1 | 8/2002 | Einsele | |
| 2002/0120116 A1* | 8/2002 | Kunsch et al. | 536/23.2 |
| 2004/0110251 A1 | 6/2004 | Grabowski et al. | |
| 2005/0079490 A1 | 4/2005 | Stuber et al. | |

FOREIGN PATENT DOCUMENTS

| | | |
|---|---|---|
| EP | 0 452 596 A1 | 10/1991 |
| EP | 0 201 184 B1 | 12/1992 |
| EP | 0 131 052 B1 | 12/1993 |
| EP | 0 497 784 B1 | 4/1999 |
| EP | 0 512 334 B1 | 9/1999 |
| EP | 0 543 942 B1 | 1/2001 |
| EP | 03812827.8 | 12/2002 |
| JP | 3109599 A | 5/1991 |
| JP | 8012551 A | 1/1996 |
| WO | WO 97/46707 | 12/1997 |
| WO | WO 97/46712 | 12/1997 |
| WO | WO 97/46714 | 12/1997 |
| WO | WO 01//94634 A3 | 12/2001 |
| WO | WO 02/14555 A2 | 2/2002 |
| WO | WO 02//070728 A2 | 9/2002 |
| WO | WO 03/002766 A2 | 1/2003 |

OTHER PUBLICATIONS

Siefring, S.D. et al, Abstracts of the General Meeting of the American Society for Microbiology 101:602 (May 2001).*

Edwards, K.J. et al, Journal of Clinical Microbiology 39(9):3047-3051 (Sep. 2001).*

Ke, D. et al, Clinical Chemistry 46(3):324-331 (2000).*

Bernard, P., et al., 1998, "Integrated Amplification and Detection of the C677T Point Mutation in the Methylenetetrahydrofolate Reductase Gene by Fluorescence Resonance Energy Transfer and Probe Melting Curves" *Analytical Biochemistry*, 255:101-107.

Bièche, I., et al., 1999, "Quantitation of *MYC* Gene Expression in Sporadic Breast Tumors with a Real-Time Reverse Transcription-PCR Assay", *Cancer Research* 55:2750-2765.

Espy, M., et al., 2000, "Diagnosis of Herpes Simplex Virus Infection in the Clinical Laboratory by Lightcycler PCR", *Journal of Clinical Microbiology*, 38(2):795-799.

Gibson,U., et al., 1996, "A Novel Method for Real Time Quantitative RT-PCR", *Genome Research*, 6:995-1001.

Klausegger A., et al., 1999, "Gram Type-Specific Broad-Range PCR Amplification for Rapid Detection of 62 Pathogenic Bacteria", *Journal of Clinical Microbiology*, 38(2):464-466.

Matthews, J., et al., 1988, "Review: Analytical Strategies for the Use of DNA Probes", *Analytical Biochemistry*, 169:1-25.

Anderson, L., et al., 2000, "Higher HIV-1 Cutoff Level Required in Cerebrospinal Fluid That in Blood to Predict Positive HIV-1 Isolation", *Journal of Medical Virology*, 62:9-13.

Angen, O., et al., 2000, "Evaluation of 5' Nuclease Assay for Detection of *Actinobacillus pleuropneumoniae*", *Journal of Clinical Microbiology*, 39(1):260-265.

Aritaki, K., et al., 2001, "A rapid monitoring system of human herpesviruses reactivation by LightCycler in stem cell transplantation", *Bone Marrow Transplantation*, 28:975-980.

Berger, A., et al., 1998, "Septicaemia in an Austrian neonatal intensive care unit: a 7-year analysis", *Acta Paediair*, 87:1066-1069.

Chayama, K., et al., 2001, "Evaluation of quantitative measurements of hepatitis C virus RNA to predict sustained response to interferon by genotype", *Journal of Virological Methods*, 95:33-45.

Giachetti, C., et al., 2002, "Highly Sensitive Multiplex Assay for Detection of Human Immunodeficiency Virus Type 1 and Hepatitis C Virus RNA", *Journal of Clinical Microbiology*, 40(7):2408-2419.

Hirakata, Y., et al., 1996, "Assessment of clinical significance of positive blood cultures of relatively low-virulence isolates", *J.Med Microbiol*, 44:195-198.

Hoorfar, J., et al., 2000, "Automated 5' Nuclease PCR Assay for Identification of *Salmonella enterica*", *Journal of Clinical Microbiology*, 38(9):3429-3435.

Lage, A., et al., 1996, "Rapid Colorimetric Hybridization Assay for Detection Amplified *Helicobacter pylori* DNA in Gastric Biopsy Specimens", *Journal of Clinical Microbiology*, 34(3):530-533.

Mas, V., et al., 1999, "Utility of Cytomegalovirus Viral Load in Renal Transplant Patients in Argentina", *Transplantation*, 67(7):1050-1055.

Monteiro, L., et al., 1997, "Evaluation of Performances of Three DNA Enzyme Immunoassays for Detection of *Helicobacter pylori* PCR Products from Biopsy Specimens", *Journal of Clinical Microbiology*, 35(11):2931-2936.

Nazzari, C., et al., 2000, "Multiplex Polymerase Chain Reaction for the Evaluation of Cytomegalovirus DNA Load in Organ Transplant Recipients", *Journal of Medical Virology*, 61:251-258.

Pelloux, I., et al., 1990, "Evaluation D'une Technique De Detection De *Legionella* SPP Par Sonde Nucleique", *Path Biol*, 39(2):150-152.

Pina, M., et al., 1998, "Detection of Point Mutations Associated with Resistance of *Helicobacter pylori* to Clarithromycin by Hybridization in Liquid Phase", *Journal of Clinical Microbiology*, 36(11):3285-3290.

Rao, M., et al., 2000, "Cytomegalovirus Infection in a Seroendemic Renal Transplant Population: A Longitudinal Study of Virological Markers", *Nephron*, 84:367-373.

Reid, S., et al., 2002, "Detection of all seven serotypes of foot-and mouth disease virus by real-time, fluorogenic reverse transcription polymerase chain reaction assay", *Journal of Virological Methods*, 105:67-80.

Serth, J., et al., 1999, "Increased Levels of Human Papillomavirus Type 16 DNA in a Subset of Prostate Cancers", *Cancer Research*, 59:823-825.

Tansuphasiri, U., et al., 2001, "Simple Microplate hybridization Assay for Detection of Amplified Products of Mycobacterium Tuberculosis", *Southeast Asian J Trop Med Public Health*, 32(4):835-843.

Lyon, E., 2001, "Mutation Detection using fluorescent hybridization probes and melting curve analysis", *Expert Rev. Mol. Diag.*, 1(1):92-101.

Bergeron, Michel G., et al., 2000, "Rapid Detection of Group B Streptococci in Pregnant Women at Delivery", New England Journal of Medicine, 343(3):175-179.

Forsman, Paivi, et al., 1997, "Identification fo staphylococcal and streptococcal causes of bovine mastitis using 16S-23S rRNA spacer regions", Microbiology, 143:3491-3500.

Li, Gou-Li, et al., 2002, "Study on identification of mycobacterum species using oligonucleotide probes based on 16s-23s rDNA internal transcribed spacer sequences", Chinese Journal of Antituberculosis, 24:12-16, English abstract only.

Mannarelli, B. M. and Kurtzman, C. P., 1998, "Rapid Identification of *Candida albicans* and Other Human Pathogenic Yeasts by Using Short Oligonucleotides in a PCR", Journal of Clinical Microbiology, 36(6):1634-1641.

Zhou, Hui, et al., 1997, "Cloning and Sequence Analysis of Two Types of rDNA 16s-23s Intergenic Spacer from *Salmonella enteritidis*", Acta Scientiarum Naturalium Universitatis Sunyatseni, 36(5):74-77, English abstract only.

Chang, Hsein Chang, et al., 2001, "Rapid Identification of Yeasts in Positive Blood Cultures by a Multiplex PCR Method", Journal of Clinical Microbiology,39(10):3466-3471.

De Silva, Deepika, et al., 1998, "Rapid Genotyping and Quantification on the LightCycler with Hybridization Probes", Biochemica, 2:12-15.

Edwards, K.J., et al., 2001, "Rapid and Accurate Identification of Coagulase-Negative Staphylococci by Real-Time PCR", Journal of Clinical Microbiology, 39(9):3047-3051.

Hein, Ingeborg, et al., 2001, "Comparison of Different Approaches to Quantify *Staphylococcus aureus* Cells by Real-Time Quantitative PCR and Application of This Technique for Examination of Cheese", Applied and Environmental Microbiology, 67(7):3122-3126.

Humar, Atul, et al., 1999, "Clinical Utility of Quantitative Cytomegalovirus Viral Load Determination for Predicting Cytomegalovirus Disease in Liver Transplant Recipients", Transplantation, 68(9):1305-1311.

Landt, Olfert, et al., 1999, "Selection of Hybridization Probe Sequences for Use with the LightCycler", Roche Applied Sciences Technical Note LC6/99:1-8. https://www.roche-applied-science.com/sis/rtpcr/lightcycler/lightcycler_docs/technical_notes/lc_06.pdf.

Loeffler, Juergen, et al., 2000, "Identification of rare *Candida* species and other yeasts by polymerase chain reaction and slot blot hybridization", Diagnostic Microbiology and Infectious Disease, 38:201-212.

Reid, S. M., et al., 2001, "Diagnosis of foot-and-mouth disease by real-time fluorogenic PCR assay", Veterinary Record, 149:621-623.

Vandecasteele, S.J., et al., 2001, "Quantification of Expression of *Staphylococcus epidermidis* Housekeeping Genes with Taqman Quantitative PCR during In Vitro Growth and under Different Conditions", Journal of Bacteriology, 183(24):7094-7101.

\* cited by examiner

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial
<220> FEATURE:
<223> OTHER INFORMATION: primer

<400> SEQUENCE: 1
tactttgttc agttttgaga ggt                                            23

<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
gcaattgaac ttattaaaaa actc                                           24

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
ctggatattg aagtaaaaag aatcaaaac                                      29

<210> SEQ ID NO 4
<211> LENGTH: 25
<212> TYPE: DNA
<213> ORGANISM: Artificial
<220> FEATURE:
<223> OTHER INFORMATION: primer

<400> SEQUENCE: 4
gatatttgaa gtaaatgtaa gtaat                                          25

<210> SEQ ID NO 5
```

```
<211> LENGTH: 21
<212> TYPE: DNA
<213> ORGANISM: Artificial
<220> FEATURE:
<223> OTHER INFORMATION: primer

<400> SEQUENCE: 5
accgagaaca ccgcgttgaa t                                              21

<210> SEQ ID NO 6
<211> LENGTH: 26
<212> TYPE: DNA
<213> ORGANISM: Artificial
<220> FEATURE:
<223> OTHER INFORMATION: primer

<400> SEQUENCE: 6
tgtacattga aaactagata agtaag                                         26

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
acgcgttatt aatcttgtga gt                                             22

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
ccgagtgaat aaagagtttt aaa                                            23

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
gcttgaattc ataagaaata atcg                                           24

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
aaaacgctgt agtattaata agagtt                                         26

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
```

```
                                            -continued atgactgaaa ggtcagaaaa taa                                              23

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
gagaggtctt gtggggcc                                                    18

<210> SEQ ID NO 13
<211> LENGTH: 13
<212> TYPE: DNA
<213> ORGANISM: Artificial
<220> FEATURE:
<223> OTHER INFORMATION: primer

<400> SEQUENCE: 13
agctcagctg gga                                                         13
```

QUANTITATIVE TEST FOR BACTERIAL PATHOGENS

BACKGROUND OF THE INVENTION

1. Field of the Invention

The invention relates to the technical field of detecting pathogenic microbial organisms. More specifically, the invention relates to the field of discriminating an infection in a clinical specimen from background by means of quantitatively amplifying specific nucleic acid sequences from said pathogenic microbial organism.

2. Prior Art Background

Infection by pathogenic bacteria, in particular if causing sepsis, is predominantly occurring and serious in intensive care units (ICU) of hospitals. The bacterium infecting the patient is in most cases unknown and cannot be determined from the symptoms. Each bacterium requires a different therapy using administration of a specific antibiotic. Presently, in routine diagnostics pathogenic bacteria, particularly Gram positive bacteria, are detected using a method including subjecting a sample of blood or other body fluid to culture to grow the bacteria, if present. This culture is maintained at conditions favouring bacterial growth for about three days. During this time, the number of bacteria and thus their nucleic acids is increased. Thereafter, the culture medium is subjected to lysis. The lysis mixture is used as the sample for hybridization reaction. The overall method takes around four days minimum until clarity on any infection of the sample by pathogenic bacteria is reached. Infection by pathogenic bacteria is very serious for the infected person. Within the first day of infection a therapy, preferably by administration of an antibiotic suitable to affect the particular infecting bacterium has to be started. Otherwise, the person is too heavily affected by the infection and may die before clarity on the infection is reached. On the other side, administration of several antibiotics simultaneously to prevent grow of all possible bacteria has to be avoided to not weaken the patient. The present methods thus are not satisfactory for routine ICU diagnostics.

Identification of pathogenic organisms such as pathogenic bacteria or fungi by means of nucleic acid based hybridization using specific hybridization probes has been known in the art already for a long time. For example, EP 0 131 052 discloses methods and probes wherein ribosomal ribonucleic acid (rRNA) sequences of a certain species or a certain group of organisms are detected directly from culture media. Detection of ribosomal target sequences is especially useful due to the fact that these sequences are amplified in-vivo, resulting in high sensitivity of the respective assay.

An improvement of nucleic acid sequence based detection of pathogenic organisms was achieved upon availability of the PCR technology. For the detection of pathogenic fungi such as *Candida* and *Aspergillus*, for example, WO 97/07238 discloses a method using generic primers for amplifying all types of fungal ribosomal 18S rDNA sequences and subsequently hybridizing with fungi species specific probes.

As an alternative to the analysis of ribosomal gene sequences, non-coding but transcribed ribosomal spacer DNA sequences like the ITS-1 region located between the 16S and the 23S rRNA genes have been used for detection and identication of several pathogenic organisms (see, for example, EP 0 452 596).

In another context, the groups of Gram positive and Gram negative bacteria have been discriminated by means of a target-dependent amplification comparable to an allele specific amplification approach (Klausegger, A., et al., J. Clin. Microbiol. 37 (1999) 464-466). On the basis of their 16S r-DNA sequences, the species investigated by Klausegger et al. differ at a given position of the 16S rRNA gene in that all investigated Gram negative bacteria contain a G-residue at a certain nucleotide position whereas all investigated Gram positive bacteria always contain a C-residue at said nucleotide position. Consequently, usage of appropriate primers having either a discriminating complementary 3'-terminal C-residue or a complementary G-residue, respectively, results in DNA amplification of either Gram positive or Gram negative sequence origin.

Further progress was made upon availability of kinetic Real Time PCR. In this type of assay, formation of PCR products is monitored in each cycle of the PCR. The amplification is usually measured in thermocyclers having additional detection means for monitoring fluorescence signals during the amplification reaction. A typical example is Roche Diagnostics LightCycler™ (Cat. No. 2 0110468). In Light-Cycler™ as well as in other Real Time PCR instruments commercially available so far, amplification products are detected by means of fluorescently labeled hybridization probes which only emit fluorescence signals when they are bound to the target nucleic acid or in certain cases also by means of fluorescent dyes that bind to double-stranded DNA. A defined signal threshold is determined for all reactions to be analyzed and the number of cycles (Cp) required to reach this threshold value is determined for the target nucleic acid as well as for the reference nucleic acids such as a standard or housekeeping gene. The absolute or relative copy numbers of the target molecule can be determined on the basis of the Cp values obtained for the target nucleic acid and the reference nucleic acid (Roche Diagnostics LightCycler™ operator manual (Cat. No. 2 0110468)).

There exist different formats for the detection of amplified DNA:

a) DNA Binding Dye Format

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Such method is described in EP 0 512 334. Preferably, only those dyes are used, like for example SYBR® Green I, which do not affect the efficiency of the PCR reaction.

All other formats known in the art require the appropriate design of a fluorescently labeled hybridization probe which only emits fluorescence upon binding to its target nucleic acid.

b) TaqMan™ Probes

A single-stranded hybridization probe is labeled with two components. When the first component, the so-called fluorescer, is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3'-exonuclease activity of the polymerase, for example Taq Polymerase, during the elongation phase. As a result the excited fluorescent component and the quencher are spatially separated from one another and thus a fluorescence emission of the first component can be measured (EP 0 543 942 and U.S. Pat. No. 5,210,015).

c) Molecular Beacons

These hybridization probes are also labeled with a first component and with a quencher, the labels preferably being located at different ends of an at least partially self-complementary probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118, 801).

d) FRET Hybridization Probes

The Fluorescence Resonance Energy Transfer (FRET) hybridization probe test format is especially useful for all kinds of homogenous hybridization assays (Matthews, J. A., and Kricka, L. J., Anal. Biochem. 169 (1988) 1-25). It is characterized by two single-stranded hybridization probes which are used simultaneously and are complementary to adjacent sites of the same strand of an (amplified) target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured only when both hybridization probes bind to adjacent positions of the target molecule to be detected.

When annealed to the target sequence, the hybridization probes must be located very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound, which is typically 10-100 Ångstrom. Particulars are well known and disclosed for example in EP 0 070 687.

Alternatively to monitoring the increase in fluorescence of the FRET acceptor component, it is also possible to monitor fluorescence decrease of the FRET donor component as a quantitative measurement of hybridization event.

In particular, the FRET hybridization probe format may be used in real time PCR, in order to detect the amplified target DNA. Among all detection formats known in the art of real time PCR, the FRET-hybridization probe format has been proven to be highly sensitive, exact and reliable (WO 97/46707; WO 97/46712; WO 97/46714). Yet, the design of appropriate FRET hybridization probe sequences may sometimes be limited by the special characteristics of the target nucleic acid sequence to be detected.

As an alternative to the usage of two FRET hybridization probes, it is also possible to use a fluorescent-labeled primer and only one labeled oligonucleotide probe (Bernard, P. S., et al., Anal. Biochem. 255 (1998) 101-107). In this regard, it may be chosen arbitrarily, whether the primer is labeled with the FRET donor or the FRET acceptor compound.

FRET hybridization probes (also called FRET-Hybprobes or FRET probes) can also be used for melting curve analysis (WO 97/46707; WO 97/46712; WO 97/46714). In such an assay, the target nucleic acid is amplified first in a typical PCR reaction with suitable amplification primers The hybridization probes may already be present during the amplification reaction or be added subsequently. After completion of the PCR-reaction, the temperature of the sample is constitutively increased. Fluorescence is detected as long as the hybridization probe is bound to the target DNA. At the melting temperature, the hybridization probe is released from their target, and the fluorescent signal is decreasing immediately down to the background level. This decrease is monitored with an appropriate fluorescence versus temperature-time plot such that the negative of a first derivative function can be calculated. The temperature value corresponding to the obtained maximum of such a function is then taken as the determined melting temperature of said pair of FRET hybridization probes.

Point mutations or polymorphisms within the target nucleic acid result in a less then 100% complementarity between the target nucleic acid and the FRET probes, thus resulting in a decreased melting temperature. This enables for a common detection of a pool of sequence variants by means of FRET-Hybprobe hybridization, whereas subsequently, different members of said pool may become discriminated by means of performing melting curve analysis. Instead of FRET hybrdization probes, Molecular Beacons may alternatively be used for melting curve analysis.

Upon the availability of Real-Time PCR and homogenous Real-Time PCR melting curve analysis, discrimination of certain types of species or strains became possible using either double stranded DNA binding dyes such as SybrGreen™I, or, alternatively, specifically designed hybridization probes hybridizing to different but similar target sequences. Hybridization probes may be used in such a way that the melting temperature of the probe/target nucleic acid hybrid is being determined. For example, Espy, M. J., et al., J. Clin. Microbiol. 38 (2000) 795-799 disclose diagnosis of Herpes simplex infections by means of amplifying a Herpes simplex sequence and subsequent analysis using FRET hybridization probes to discriminate between the HSV Type I and the HSV Type II genotype.

Furthermore, WO 01/48237 suggests in general the connection of amplification and temperature dependent hybridization in order to detect different pathogenic species. Yet, WO 01/48237 does not teach any methods or conditions which enable for an exclusive detection of pathogenic organisms, but to not detect any non pathogenic organism.

Even the presently used methods including in-vitro amplification of specific bacterial species and subsequent detection of said bacterium are not useful for cases where urgent diagnostics is needed, for example in ICU, because for each bacterium an amplification reaction and a detection reaction have to be performed. This requires that a large amount of sample volume, such as blood, has to be drawn from each patient. In ICU large sample volumes from severely infected patients are not available.

Moreover, all kind of blood cultures and the molecular diagnostic methods disclosed above are exclusively qualitative methods. Due to false positive results from contaminations, however, blood culture experiments as well as molecular analysis methods need to be repeated several times in order to obtain a definitve diagnostic result which can serve as a basis for an appropriate diagnostic treatment. False postive results are very often due to Coagulase negative Staphylococci contaminants.

Thus, there is a need in the art to provide methods which are specifically applicable for detecting and quantifying relevant pathogenic organisms of interest. In particular, there is a need in the art for a method which enables for the discrimination between a systemic infection and a false positive signal due to contamination or background DNA in body fluids.

BRIEF DESCRIPTION OF THE INVENTION

The problem disclosed above is resolved by methods and compounds disclosed and claimed in the present application.

In general, the present invention is directed to a method for analyzing the presence of a bacterial pathogen in a clinical sample comprising the steps of at least partially isolating nucleic acid from said sample, characterized in that said nucleic acid is selected from a group consisting of either total nucleic acid, total DNA or total RNA quantifying the amount of nucleic acid comprising a preselected sequence which is specific for said bacterial pathogen determining whether said amount of nucleic acid comprising a preselected sequence which is specific for said bacterial pathogen exceeds a first predetermined cut off value.

Additionally, it can be determined whether said amount of nucleic acid comprising a preselected sequence which is specific for said pathogen remains under a second predetermined cut off value.

Preferably, the step of quantifying the amount of said nucleic acid is performed by means of amplification, preferably by means of a Polymerase Chain Reaction, and most preferably by means of a Polymerase Chain Reaction which is monitored in real time.

In many cases, monitoring of a Polymerase Chain Reaction in real time is preformed by means of an approriate hybridization probe. If this is the case, it is also possible to monitor temperature dependence of hybridization between the probe and the amplified target nucleic acid. In the context of the present invention, said temperature dependence is indicative for the presence of a group of predetermined species of said bacterial pathogen.

In one embodiment, the specific bacterial pathogen to be detected is selected from a group consisting of Coagulase negative Staphylococci and Enterococci.

In another embodiment, which is not mutually exclusive with the embodiment disclosed above, the determined amount of nucleic acid comprising a preselected sequence which is specific for said bacterial pathogen is indicative for a sepsis event if it exceeds said preselected cut off value.

The method according to the new invention is applicable for a variety of clinical samples, which are preferably body fluids. Highly prefered as a clinical sample is whole blood.

DETAILED DESCRIPTION OF THE INVENTION

The present invention provides methods and compounds especially suitable for the definitive diagnosis of a pathogenic infection, in particular of an infection of of Gram positive bacteria. Especially when combined with Real Time PCR technology such as LightCycler™ system, the present invention enables for a rapid and definitve diagnosis of an infectious agent causing sepsis, which is of outstanding importance in many clinical environments.

In general, the present invention is directed to a method for analyzing the presence of a bacterial pathogen in a clinical sample comprising the steps of at least partially isolating nucleic acid from said sample, characterized in that said nucleic acid is selected from a group consisting of either total nucleic acid, total DNA or total RNA, quantifying the amount of nucleic acid comprising a preselected sequence which is specific for said bacterial pathogen, and determining whether said amount of nucleic acid comprising a preselected sequence which is specific for said bacterial pathogen exceeds a first predetermined cut off value.

Thus, the inventive method allows for a convenient, one step differentiation between an actual pathogenic infection and a putative contamination.

By means of setting a cut off value, the quantitative data obtained are divided into two classes. One class of data exceeding said cut off value for the amount of nucleic acid that is being quantitatively detected is clearly indicative for a pathogenic infection. The second class of data which remain under said cut off value is indicative for the absence or non confirmation of a pathogenic infection.

In this context, the term "cut off value" is further defined as a value which can clearly higher and can be discriminated from values due to background signaling caused by the intrinsic characteristics of the detection principle, which are also obtained in the absence of any bacterial contamination in the sample.

Predetermination of an appropriate cut off value depends on the mode of quantification that has been chosen and can be done by a person skilled in the art. In this regard, quantitative data obtainable from a large number of clinical samples from patients that have been proven to suffer from a systemic infection of a bacterial pathogen are compared with quantitative data from a large number of samples from individuals that have been proven to be free of any pathogenic infection. The optimal cut off value is then set in such a way that the numbers of false positive and false negative results are minimized.

The second class of quantitative data can be subdivided into two subclasses by means of setting a second cut off value. Under these conditions, one class of data remaining under said second cut off value is clearly indicative for the absence of a pathogenic infection, the second class of data exceeding said second cut off value but remaining under said first cut off value represents those cases, where a pathogenic infection is not confirmed but on the other hand can also not be excluded.

Quantification of the amount of nucleic acid comprising a predetermined sequence is advantageoulsy done by means of amplification, preferably by means of a Polymerase Chain Reaction, and most preferably by means of a Polymerase Chain Reaction which is monitored in real time.

There are many different absolute or relative methods of quantitative PCR known in the art, all of which can be applied within the scope of the present invention. A distinction is made between two different variants:

In the so-called relative quantification the ratio of a certain target nucleic is determined relative to the amount of a reference nucleic acid which is assumed to be present in all samples with the same quantity. Alternatively, the absolute amount of a certain nucleic acid can be determined with the aid of standard nucleic acids of a known copy number and amplification of a corresponding dilution series of this standard nucleic acid.

When using external standards, the standard and target nucleic acid are amplified in separate reaction vessels. In this case a standard can be used with an identical sequence to the target nucleic acid. However, systematic errors can occur in this type of quantification if the nucleic acid preparation to be analysed contains inhibitory components which impair the efficiency of the subsequent PCR reaction. Such errors can be excluded by using internal standards i.e. by amplifying the standard and target nucleic acid in one reaction vessel. However, a disadvantage of this method is that standards have to be used that have different sequences compared to the target nucleic acid to be analysed in order to be able to distinguish between the amplification of the standard and target nucleic acid. This can in turn lead to a systematic error if the amplification or detection efficiency is different.

In the case of real time PCR, a defined signal threshold is determined for all reactions to be analysed and the number of cycles (Cp) required to reach this threshold value is determined for the target nucleic acid as well as for the reference nucleic acids. The absolute or relative copy numbers of the target molecule can be determined on the basis of the Cp values obtained for the target nucleic acid and the reference nucleic acid (Gibson, U. E., et al., Genome Res. 6 (1996) 995-1001; Bieche, I., et al., Cancer Res. 59 (1999) 2759-2765; WO 97/46707; WO 97/46712; WO 97/46714).

In the context of the present invention, the specific terms used above are defined as follows:

The term "bacterial pathogen" means that a bacterial organism may affect the health status of a human being, if that human being is infected by that bacterium. The gist of the invention is directed to the identification of bacteria causing sepsis.

The term "analyzing the presence of a bacterial pathogen" is used to describe a method to determine the abundance of a predetermined group of pathogenic bacteria in the sample. The quantitative output or result of the analysis is an absolute or relative value of the concentration of a nucleic acid sequence, which is specific for said pathogen. This will allow subsequently for a discrimination between background signaling due to contamination effects and real pathogenic infections and thius enable for a decision on whether to apply a selective antibiotic therapy.

The term "predetermined group of pathogenic bacteria" is used to describe a predefined group of pathogenic bacteria which are of interest for a particular task. In one embodiment, said predetermined group of bacteria may be a phylogenetic taxon such as a genus, a species, or a certain type of strain. In another embodiment, such a predetermined group may comprise the clinically relevant members of two or more genera. Alternatively, all known clinically relevant members of a certain genus may constitute such a predetermined group. Alternatively, all known clinically relevant members or strains or isolates of a certain species may constitute such a predetermined group. The predetermined group can also contain taxonomic sub-groups of different genera, mixed with strains from other genera or species.

In a particular embodiment, the bacterial pathogens to become detected are pathogenic gram positive bacteria such as for example but not limited to Coagulase negative Staphylococci or any kind of pathogenic Enterococci. Gram positive bacteria to become detected by the present invention may be either one, several or all of the following species: *Streptococcus pneumoniae, Streptococcus pyogenes, Streptococcus agalactiae, Streptococcus viridans* group (*S. mitis, S. mutans* and *S. bovis*), *Enterococcus faecium, Enterococcus faecalis, Staphylococcus aureaus, Staphylococcus epidermidis* and *Staphylococcus haemolyticus*.

In particular, the determined amount of nucleic acid comprising a preselected sequence which is specific for said bacterial pathogen is indicative for a sepsis event. As it is known in the art, sepsis events are systemic infectious diseases of the blood vessel system, which have a severe impact on the health status of the patient.

The term "pre-selected nucleic acid sequence" shall mean a distinct target nucleic acid region present in all organisms intended to be amplified and detected. Depending on the embodiment, there may exist some sequence variations between the sequences of different organisms. In other words, it is always the same gene or the same homologous sequence of each organism, which is amplified. An example of such a region is the 16S/23S rDNA spacer region, i.e. the region between the sequences coding for the 16S and the 23S rRNA, or a part thereof. More preferably, the preselected nucleic acid sequence region contains at least 20, even more preferred more than 40 contiguous nucleobases from the 16S/23S spacer region of the organisms to be amplified. This region contains evolutionary conserved as well as hypervariable sequences, which allow for a flexible design of both, genus and species specific primers and probe. The region is contained within the region defined by the primer binding sites on the nucleic acid.

The term "specific" is used to describe the characteristic of a subject (for example in methods, steps or reagents) that the subject is directed to only a particular and defined result. For example, a method for the detection of a particular species is considered to be specific, if only this species, but not other species are detected. Specific hybridization of a probe with a target is a hybridization which only occurs between the probe and the target, but not with other nucleic acids.

In this context, the overall method of the present invention is preferably substantially specific regarding the identification and quantification of the organism. Organisms not being a member of the predetermined group are not identified, because the steps performed with the reagents are adjusted to not detect and quantify organisms not belonging to that group.

Preferably, the step of quantifying the amount of said nucleic acid is performed by means of amplification, preferably by means of a Polymerase Chain Reaction. The term "amplification" shall mean a reaction or a series of reactions that amplifies, a target sequence—if present in the clinical specimen—by means of using a set of amplification primers usually consisting of a forward and reverse primers for a nucleic acid amplification reaction from a specimen containing DNA. The specificity of said amplification depends upon the group selected and is governed by the specificity of the primers used. Preferably, amplification is obtained by means of a polymerase chain reaction (PCR) using a thermostable DNA polymerase. In one embodiment, the amplification is specific for bacteria generally; i.e. viruses are not amplified in substantive amounts.

The term "set of amplification primers" shall mean at least two (extendable) oligonucleotides or oligonucleotide derivatives, i.e. at least one (forward) primer binding to a first strand of the target nucleic acid and at least a second (reverse) primer binding to the opposite strand of the target nucleic acid sequence to be amplified. Moreover, the positioning of the primers is designed in such a way that template dependent extension of each primer generates an extension product which itself comprises a primer binding site to which the other primer can hybridize.

In most cases, it is sufficient to use a pair of two amplification primers consisting of one forward primer and one reverse primer. Yet, in some cases there may exist some minor sequence variants in the sequences of the primer binding sites of different sequences of different pathogenic Gram positive bacteria to be identified. Thus it may be impossible to amplify the sequences of all members by just using one forward and one reverse primer. For those cases, a set of amplification primers may consist of 1, 2, or more forward primers and/or 1, 2 or more reverse primers, which are similar and bind to homologous sequences, but differ from each other by one, two, three or several mononucleotide-, dinucleotide- or trinucleotide exchanges, deletions, or additions.

Moreover, it is also within the scope of the invention, if two, three or multiple sets of amplification primers capable of amplifying different pre-selected nucleic acid sequence regions are used. In this case, said different pre-selected nucleic acid sequences may not necessarily be related to each other in sequence. Yet, it is also within the scope of the present invention, if the different pre-selected nucleic acid sequence regions are at least partially or almost completely overlapping.

In general, the design of amplification primers is performed on the basis of available sequence information with regard to the pre-selected target nucleic acid sequence regions of the pathogenic bacteria to be amplified as well as with regard to the homologous sequences of those Gram positive and Gram negative bacteria, which shall not be amplified. More precisely, the set or sets of amplification primers are selected in such a way that there is a maximum sequence complementarity with respect to all target nucleic acid sequences of the selected predetermined group of pathogenic bacteril pathogena, and, on the other hand, a minimum sequence complementarity with respect to nucleic acid sequences of all other non-selected Gram positive bacteria and Gram negative bacteria, i.e. those not belonging to the predetermined group or not being pathogenic, as well as fungi.

Preferably, the step of quantifying the amount of said nucleic acid is performed by means of a Polymerase Chain Reaction which is monitored in real time. In most cases, monitoring of a Polymerase Chain reaction in real time is preformed by means of an appropriate hybridization reagent. If this is the case, it is also possible to monitor temperature dependence of hybridization between the probe and the amplified target nucleic acid. In the context of the present invention, said temperature dependence is indicative for the presence of a predetermined subgroup of said bacterial pathogen.

The term "hybridization reagent" is used to describe a reagent capable of hybridizing to products of amplification within the preselected nucleic acid sequence region; i.e. on at least one strand of the amplicon(s). The reagent can comprise one or more probes, which preferably are single stranded or are made single stranded prior to hybridization. Preferably the reagent is a single stranded nucleic acid hybridization probe system, comprising usually one or two nucleic acids which are capable of hybridizing to one strand of the double stranded amplified target nucleic acid. Depending on the type of detection format, it is in most cases advantageous if the hybridization reagent is appropriately labelled with a detectable entity, such that by detection of said label, the amplicon/hybridization-reagent hybrid can be detected.

In a preferred embodiment, the hybridization reagent is labelled with a fluorescent entity such that hybridization can be detected in commercially available Real Time PCR instruments. Reagents useful for this are disclosed in the documents mentioned above describing the different formats for the detection of amplified DNA.

The hybridization reagent in a simple case may be an oligonucleotide probe. For example, the Molecular Beacon Format (U.S. Pat. No. 5,118,801) may be applied. Alternatively, it is also possible to use appropriate single labeled oligonucleotides (WO 02/14555). These references are cited to incorporate their content regarding reagents and processes of detection.

More preferably, the hybridization reagent is composed of two adjacently hybridizing oligonucleotides, appropriately labelled such that together they can act according to the FRET-Hybprobe detection format as disclosed above (WO 97/46707; WO 97/46712; WO 97/46714).

Furthermore, in this context, the term "FRET pair" is defined as a pair of fluorescent labels that act together to create a FRET process, i.e. it consists of a FRET donor moiety and a FRET acceptor moiety.

Similar to the design of a set of amplification primers, the design of a hybridization reagent or multiple hybridization reagents is also performed on the basis of all available sequence information with regard to the pre-selected target nucleic acid sequences to be amplified and detected as well as with regard to the homologous sequences of those pathogenic bacteria, which shall not be detected. More precisely, the sequences of the hybridization reagent(s) are selected in such a way that there is maximum sequence complementarity with respect to all target nucleic acid sequences of the selected predetermined group of pathogenic bacteria, and, on the other hand, a minimum sequence complementarity with respect to all homologous nucleic acid sequences of all other non selected Gram positive bacteria or Gram negative bacteria.

In a particular embodiment of the present invention, if monitoring of a Polymerase Chain reaction in real time has been preformed by means of an approriate hybridization probe, temperature dependence of hybridization between the probe and the amplified target nucleic acid is monitored and the respective melting temparature is determined.

In this context, the term "monitoring temperature dependence of hybridization" shall mean that a characteristic of the reaction mixture is monitored for a certain period of time or in intervals, as required for an intended accuracy of the assay, which changes with and is dependent on the dissociation of a hybrid. Usually, and in conjunction with hybridization assays using labelled probes, the characteristic is a signal influenced by the label on the probe and changed upon hybridization of the probe to an amplicon/target.

The melting temperature (Tm) of a hybrid is defined as the temperature at which the maximum of a first derivative of the hybridization versus temperature signal plot is reached. The Tm is a characteristic of a hybrid depending upon complementarity of the strands. In the present invention, the annealing temperature of the probe(s) is preferably lower than the melting temperature of the primers used. A change of characteristics will particularly occur at the or around the melting temperature of each hybrid. The melting temperature is determined by the particular hybridization reagent and the corresponding region at each target to which the reagent binds. In particular, in the method of the present invention, the melting temperature is determined, at which the probe is dissociating from the hybridization complex formed with the target nucleic acid/amplicon. In this context, it is important to note that the melting temperature (Tm) is depending on several factors independent from the actual target nucleic acid sequence itself, such as salt concentration, length and GC-content of the probe. Yet in addition, the melting temperature strongly depends on the number of mismatches, i.e. degree of complementarity between the probe and the target sequence. As a consequence, different melting temperatures are obtained for target sequences found in different strains of a distinct species or different species of a distinct genus.

In the context of the present invention, said temperature dependence is indicative for the presence of a predetermined subgroup of bacterial pathogen. The term "predetermined sub-group of bacterial pathogen" is used to describe a part or the whole of the predetermined group of pathogenic organisms. Preferably, the predetermined subgroup is only a small part of all pathogenic organisms. The members of the group and the subgroup can be chosen from one genus, but can also be chosen from different genera. In case the predetermined group is represented by all pathogenic and clinically relevant members of a genus, a respective sub-group may contain all respective pathogenic members of a certain species. Similarly, if said predetermined group consists of all clinically relevant members of a certain species, then the sub-group may consist of all members of a specific strain.

As a consequence, the design of the hybridization reagent needs to take into account that a discrimination of several target sequence variations is possible on the basis of monitoring temperature dependence of hybridization. This particular embodiment present invention requires different melting temperatures for hybridization of a hybridization reagent to different target sequence variants originating from different pathogenic bacteria. Thus, the sequences of a hybridization reagent according to the invention are designed in such a way that the calculated melting temperatures (calculated by methods known in the art) of the different hybridization reagent/target sequence hybrids differ from each other by at least 2° C., preferably by 4° C. and most preferably by at least 6° C.

The method according to the new invention is applicable for a variety of clinical samples, which is suspected to contain a pathogenic bacterium. Examples of such clinical samples are body fluids such as whole blood, serum and cerebrospinal fluid. Most preferred are whole blood samples, since these samples can be directly analyzed in order to obtain relevant information on the presence or absence of a sepsis event.

In order to achieve a sufficient sensitivity for detecting an infection, the method of the invention requires an at least partial purification of the nucleic acid from the original sample. The nucleic acid to be isolated can either RNA or DNA or a mixture thereof. As the most preferably embodiment of the invention uses bacterial DNA for the final identification of the pathogenic organism, it is not required that the clinical specimen contains RNA. Therefore, it is not necessary to partially or even completely isolate RNA from the clinical sample. The isolation of DNA from the clinical sample should be as sufficient and complete as necessary to receive a signal with a positive control.

Particularly, the nucleic acids are separated from proteins, sugars and salts present in the original sample. Any purification method known in the art may be used in the context of the present invention. Preferably, methods are applied which result in an essentially complete purification of the total DNA to be analyzed from other components of the clinical sample. At least, purification should be performed to such an extend that without any further substantial dilution, nucleic acid sequences in aliquots of the specimen can successfully be amplified in an in-vitro amplification, such as PCR. In purification, any compounds substantially inhibiting polymerases are removed from the nucleic acids. Particularly useful methods of nucleic acid isolation are disclosed in WO 96/41811.

The result of said at least partial puification usually is a fluid comprising nucleic acids from the original clinical sample and in addition reagents added during the isolation step, like buffers. In step b), the clinical specimen or a part thereof are subjected to one or more amplification reactions. The amplification and detection reactions can comprise one or more steps. Both, amplification and detection reactions are known in the art. The amplification is done using an in-vitro method, preferably PCR (EP 0 201 184). In the following, reference is made to PCR, but it is understood that other in-vitro methods are suitable, too. The result of the amplification reaction is the production of a large number of extension products of said primers, predominantly having a sequence reaching from the 5'-terminal position of one primer to the 5'-terminal position of the other primer. Those nucleic acids produced are usually called "amplicons".

In order to avoid false negative results due to inhibitory residual components which may be present in the clinical specimen and for quantification purposes, it has been proven to be particular advantageous, if an internal control template is added. Usually, said control template comprises a known sequence with primer binding sites complementary to at least one set of amplification primers used for amplification of the target nucleic sequences to be detected. Consequently, said set of amplification primers is also capable of priming amplification of said selected sequence of the control template. Details of using internal standards, particularly for quantification, are disclosed in EP 0 497 784.

It has proven to be advantageous if the method according to the invention is performed using an aliquot of a clinical specimen which has a volume of between 10 and 100 µl. Thus, the method of the present invention can be performed with a sufficient sensitivity, if only a small amount of a clinical sample such as whole blood or serum is available.

Yet, eventually, the results of the inventive method or any other method known in the art may become affected by a high background of human genomic DNA present in a clinical specimen. If this is the case, a pre-amplification step according to WO 01/94634 may be performed, characterized in that selectively non-human DNA sequences are selectively amplified.

The following examples, references, sequence listing and figures are provided to aid the understanding of the present invention, the true scope of which is set forth in the appended claims. It is understood that modifications can be made in the procedures set forth without departing from the spirit of the invention.

Samples

Whole blood samples from suspected sepsis patients being culture-positive have been used in our study. In addition, whole blood from healthy donors and culture-negative patients have been processed and analyzed. The DNA of all samples have been extracted using 1 ml of whole blood.

Whole blood was subjected to a sample preparation in which the nucleic acids were released and purified from the other components of the sample. This was done using Mag-NAPure™ LC and MagNA Pure LC DNA isolation kit III (bacteria, fungi)(Roche Diagnostics GmbH, Germany, Cat No. 3 264 785). The sample preparation yielded in a specimen containing the nucleic acids in elution buffer.

Hardware/Software

LightCycler™ with Software version 4.49 (Roche Diagnostics GmbH, Germany) The commercially available instrument was modified in such a way that the rotor was adapted to hold 100 µl capillaries. The fluorimeter of said instrument was altered in such a way that it was composed of 4 instead of 3 photohybrids, and fluorescence emission could be detected at 610 nm, 640 nm, 670 nm and 705 nm.

Reagents

All oligonucleotides mentioned herein were prepared by chemical synthesis. The reagents for attaching labels can be purchased from Roche Diagnostics GmbH (LightCycler Red 640 NHS Ester Cat. No. 2015161; LightCycler Red 705 Phosphoramidite Cat. No. 2157594; LightCycler Fluorescein (abbreviated 'F' in the following) CPG Cat. No. 3113906). The use of those reagents is described in Biochemica No. 1

(2001), p. 8-13. Cy5-NHS Ester can be obtained from Amersham upon request. LC-Red 610-NHS ester has an emission maximum at 610 nm and was synthesized according to standard protocols using a fluorescent dye as disclosed in U.S. Pat. No. 5,750,409.

All reagents need to be checked for contamination by the organisms to be detected. Only reagents free of those organisms and the nucleic acids originating therefrom can lead to an optimum sensitivity.

FastStart polymerase and FastStart Master were generally used as recommended in the LightCycler-FastStart-DNA Master Hybridization Probes Kit (Roche Diagnostics GmbH Cat. No. 2239272).

Primers and probes directed against the ITS-1 region between the 18s and the 23s rDNA according to the following table were used.

|  | Oligo-Name | Sequenz | Info |
|---|---|---|---|
| Enterococcus | Enterococ FP | 5'-TAC-TTT-GTT-CAG-TTT-TGA-GAG-GT-3' Seq Id no 1 | Forward Primer |
|  | Enterococ RP | 5'-GCA-ATT-GAA-CTT-ATT-AAA-AAA-CTC-3' Seq Id no 2 | Reverse Primer |
|  | Enterococ Fluos1 | 5'-CTG-GAT-ATT-GAA-GTA-AAA-AGA-ATC-AAA-AC-X-3' Seq Id no 3 | Fluos Probe I |
|  | Enterococ Fluos2 | 5'-GAT-ATT-TGA-AGT-AAA-TGT-AAG-TAA-T-X-3' Seq Id no 4 | Fluos Probe II |
|  | Enterococ Red610 | 5'-LCRed$_{610}$-ACC-GAG-AAC-ACC-GCG-TTG-AAT-p-3' Seq Id no 5 | Red 610 Probe |
| Staphylococcus | StaphP30 FP | 5'-TGT ACA TTG AAA ACT AGA TAA GTA AG-3' Seq Id no 6 | Forward Primer |
|  | StaphP31 RP | 5'-ACG CGT TAT TAA TCT TGT GAG T-3' Seq Id no 7 | Reverse Primer |
|  | Staph Fluos | 5'-CCG AGT GAA TAA AGA GTT TTA AA-X 3' Seq Id no 8 | Fluos Probe I |
|  | Staph Red640 | 5'-LCRED$_{640}$-GCT TGA ATT CAT AAG AAA TAA TCG-3' Seq Id no 9 | Red 640 Probe |
| Streptococcus | Strep Fluos 1 | 5'-AAA ACG CTG TAG TAT TAA TAA GAG TT-X-3' Seq Id no 10 | Fluos Probe I |
|  | Strep LC Red670 | 5'-LCRed670-ATG ACT GAA AGG TCA GAA AAT AA-3' Seq Id no 11 | Red 670 Probe |
|  | Strep A92 Fluos | 5'-GAG AGG TCT TGT GGG GCC-X-3' Seq Id no 12 | Fluos Probe 2 |
|  | Strep S93 LCRed705 | 5'-LCRed705-AGC TCA GCT GGG A-3' Seq Id no 13 | Red 705 Probe |

With these oligonucleotides, a reaction mix was prepared as follows:

| Reagent | Used volume | Final concentration |
|---|---|---|
| 10 × LC-FastStart DNA Master Hybridization Probe reagent | 10 µl | Taq DNA Polymerase, reaction buffer 1 mM MgCl$_2$, dNTPs |
| MgCl$_2$ (25 mM) | 10 µl | 3.0 mM |
| UNG (1U/µl) | 1 µl | 2U |
| Primer Enterococ FP (20 pmol/µl) | 2.5 µl | 0.5 µM |
| Primer Enterococ RP (20 pmol/µl) | 2.5 µl | 0.5 µM |
| Primer StaphP3O (20 pmol/µl) | 2.5 µl | 0.5 µM |
| Primer StaphP31rev (20 pmol/µl) | 2.5 µl | 0.5 µM |
| Staphylococci: Staph Fluos (20 pmol/µl) | 1 µl | 0.2 µM |
| Staphylococci: Staph Red640 (20 pmol/µl) | 1 µl | 0.2 µM |
| Enterococci: Entero-Fluos I (20 pmol/µl) | 1 µl | 0.2 µM |
| Enterococci: Entero Fluos II (20 pmol/µl) | 1 µl | 0.2 µM |
| Enterococci: Entero Red610 (20 pmol/µl) | 1 µl | 0.2 µM |
| Streptococcus Strep Fluos1 (20 pmol/µl) | 1 µl | 0.2 µM |
| Streptococcus: Strep Red670 (20 pmol/µl) | 1 µl | 0.2 µM |
| Streptococcus: Strep Fluos2 (20 pmol/µl) | 1 µl | 0.2 µM |
| Streptococcus: Strep Red705 (20 pmol/µl) | 1 µl | 0.2 µM |
| Water (PCR grade, Roche) | Adjusted |  |
| Target (purified DNA after sample prep) | 50 µl |  |
| Total volume | 100 µl |  |

Method

A LightCycler-run was performed using the following thermocycling and melting temperature profile:

|  | Cycles | time (sec) | Temp (° C.) | Slope(° C.) |
|---|---|---|---|---|
| Denaturation | 1 | 600 | 95° C. | 20 |
| Amplification | 10 | 10 | 95 | 20 |
|  |  | 25 | 60 | 20 |
|  |  | 50 | 72 | 20 |
| Amplification | 35 | 10 | 95 | 20 |
|  |  | 25 | 50 | 20 |
|  |  | 10 | 72 | 20 |
| Melting curve | 1 | 60 | 95 | 20 |
|  |  | 60 | 40 | 20 |
|  |  | 0 | 80 | 0.1 |
| Cooling | 1 | 30 | 40 | 20 |

EXAMPLES

Example 1

Results Coagulase Negative Staphylococci

Figure 1:
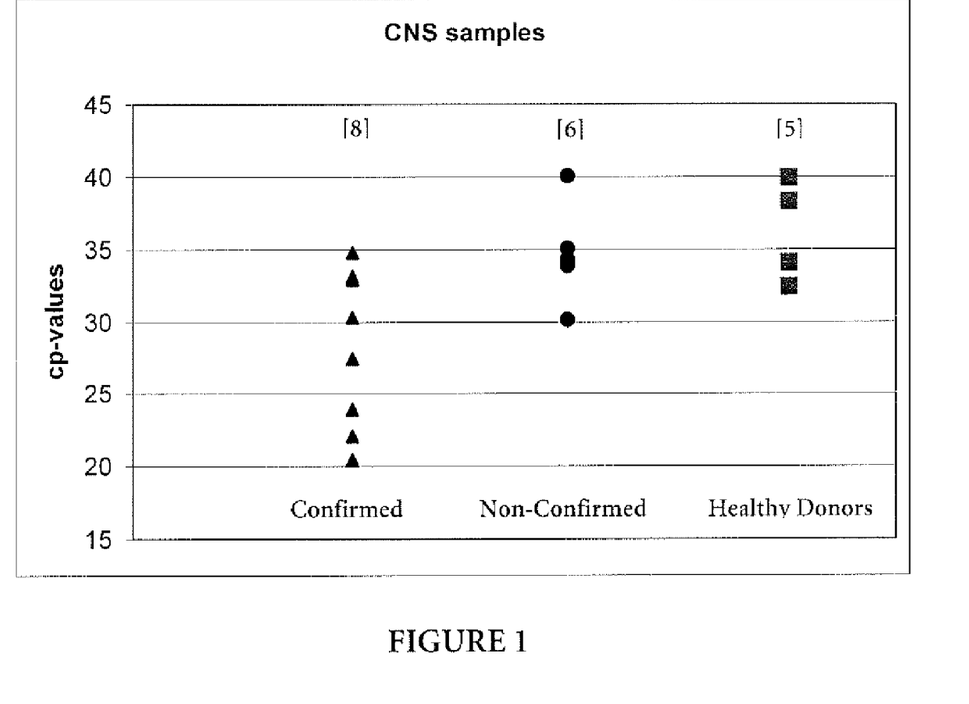
FIG. 1 Scattered blot indicating cp-values of confirmed coagulase negative *staphylococcus* samples, non-confirmed coagulase negative *staphylococcus* samples and healthy donors.

Results are summarized in scattered blot of FIG. 1, indicating the Cp values (cycle number) obtained for a group of samples from patients suffering from a *Staphylococcus* infection confirmed by blood culture analysis, a group of samples from patients suffering from a *Staphylococcus* infection which was not confirmed by blood culture analysis, and a control group of samples isolated from healthy donors. In general, cp-values are a measure of the initial pathogenic load in a given sample.

As can be seen from FIG. 1, the majority of the samples being confirmed for CNS infection have a much lower cp-value. Thus, these samples reveal a higher initial DNA titer of this pathogenic bacterium. As a consequence, the mean value between patients with a confirmed CNS infection is clearly distinguishable from patients only suspected (non-confirmed) for CNS infections or even from healthy donors.

Example 2

Results Enterococci

Figure 2:
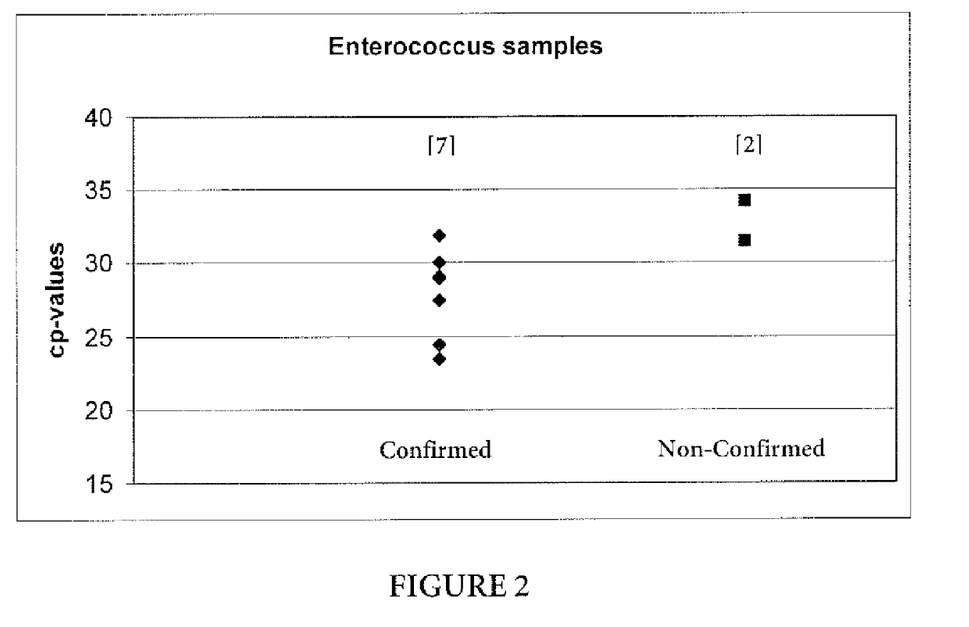
FIG. 2 Scattered blot indicating cp-values of confirmed and not confirmed *Enterococcus* infections.

Results are summarized in scattered blot of FIG. 2, indicating the Cp values (cycle number) obtained for a group of samples from patients suffering from an *Enterococcus* infection confirmed by blood culture analysis, and a group of samples from patients putatively suffering from an *Enterococcus* infection which was not confirmed by blood culture analysis Thus, a similar differentiation is possible for *Enterococcus* infections and other pathogenics, since it can be expected that the samples of the control group represent cases without a systemic *Enterococcus* infection.

We claim:

1. Method for detecting the presence of a bacterial pathogen in a clinical sample comprising the steps of:
   at least partially isolating nucleic acid from said sample, wherein said nucleic acid is selected from a group consisting of total nucleic acid, total DNA and total RNA,
   quantifying an amount of nucleic acid from said sample comprising a 16S/23S rDNA spacer region which is specific for said bacterial pathogen by means of Polymerase Chain Reaction monitored in real time by means of a group of hybridization probes, wherein said group of hybridization probes comprises the probes of each of SEQ ID NOS: 3, 4, 5, 8, 9, 10, 11, 12, and 13,
   monitoring temperature dependence of hybridization of said multiple hybridization probes to said 16S/23S spacer region, wherein said monitoring temperature dependence of hybridization is effective to detect the presence of a group of predetermined species of said bacterial pathogen, and
   performing at least two of:
   a) determining whether said amount of nucleic acid from said sample comprising the 16S/23S rDNA spacer region is above a first predetermined cut off value,
   b) determining whether said amount of nucleic acid from said sample comprising the 16S/23S rDNA spacer region is less than a second predetermined cut off value which is less than said first predetermined cut off value, and
   c) determining whether said amount of nucleic acid from said sample comprising the 16S/23S rDNA spacer region is less than said first predetermined cut off value and above said second predetermined cut off value,
   wherein said amount of nucleic acid from said sample comprising the 16S/23S rDNA spacer region is indicative of the presence of said bacterial pathogen if said amount of nucleic acid from said sample comprising the 16S/23S rDNA spacer region is above said first predetermined cut off value,
   wherein said amount of nucleic acid from said sample comprising the 16S/23S rDNA spacer region is indicative of the absence of said bacterial pathogen if said amount of nucleic acid from said sample comprising the 16S/23S rDNA spacer region is less than said second predetermined cut off value, or
   wherein said bacterial pathogen is not confirmed nor excluded if said amount of nucleic acid from said sample comprising the 16S/23S rDNA spacer region is above said second predetermined cut off value but is less than said first predetermined cut off value.

2. Method according to claim 1, wherein said clinical sample is whole blood.

* * * * *